(12) United States Patent
Matthiesen

(10) Patent No.: US 6,518,241 B2
(45) Date of Patent: Feb. 11, 2003

(54) SHOCK HEAT TREATMENT OF POLYPEPTIDES

(75) Inventor: Finn Matthiesen, Bronshoj (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/850,452

(22) Filed: May 7, 2001

(65) Prior Publication Data

US 2002/0010129 A1 Jan. 24, 2002

Related U.S. Application Data

(63) Continuation of application No. PCT/DK01/00234, filed on Apr. 6, 2001.
(60) Provisional application No. 60/197,650, filed on Apr. 17, 2000.

(30) Foreign Application Priority Data

Apr. 6, 2000 (DK) .......................... 2000 0573

(51) Int. Cl.⁷ .................. A61K 38/00; A61K 38/28; A01N 37/18
(52) U.S. Cl. ................ 514/2; 514/2; 514/12; 514/13; 514/14; 530/303; 530/308; 530/324; 530/350; 530/365; 530/366; 435/69.1

(58) Field of Search ................. 514/2, 12, 13, 514/14; 530/303, 308, 324, 350, 365, 366; 435/69.1

(56) References Cited

U.S. PATENT DOCUMENTS

| | | | | |
|---|---|---|---|---|
| 4,183,849 A | * | 1/1980 | Hansen et al. | 260/112.7 |
| 4,782,138 A | | 11/1988 | Rialland et al. | 530/366 |
| 4,880,913 A | | 11/1989 | Doleschel et al. | 530/387 |

FOREIGN PATENT DOCUMENTS

| | | |
|---|---|---|
| DE | 3337076 A1 | 5/1985 |
| EP | 0 577 147 A2 | 1/1994 |

* cited by examiner

Primary Examiner—Karen Cochrane Carlson
Assistant Examiner—Chih-Min Kam
(74) Attorney, Agent, or Firm—Reza Green

(57) ABSTRACT

The present invention relates to a method of shock heat treatment of polypeptides, to a stable polypeptide in a fluid medium, to a pharmaceutical composition comprising a stable polypeptide, to use of shock heat treatment for stabilizing a polypeptide, and to an industrial or large scale method of manufacturing a polypeptide comprising applying shock heat treatment during the manufacturing of the polypeptide.

3 Claims, 1 Drawing Sheet

SHOCK HEAT TREATMENT OF POLYPEPTIDES

CROSS REFERENCE TO RELATED APPLICATIONS

Figure 1:
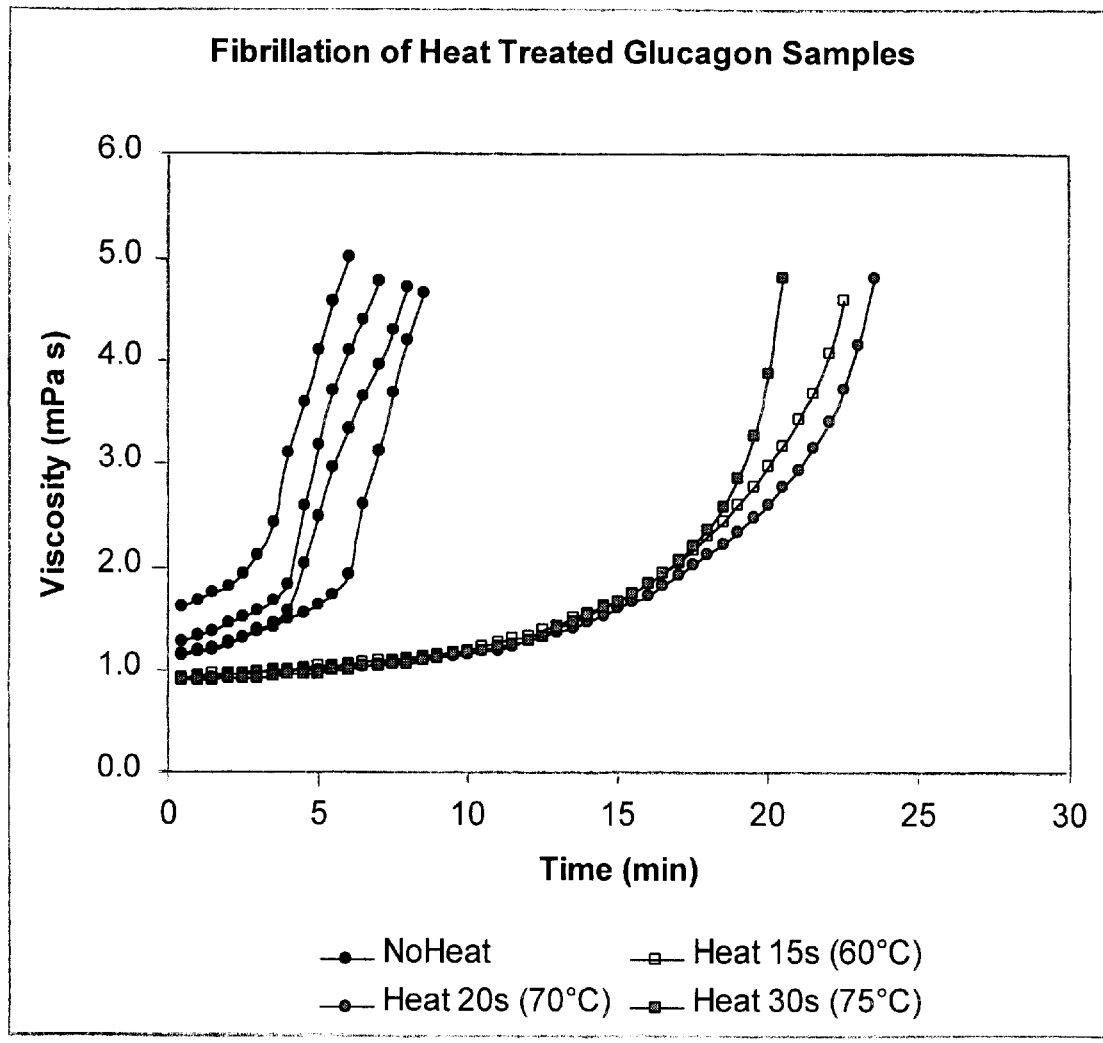

This application is a continuation of PCT/DK01/00234 filed on Apr. 6, 2001, and claims priority under 35 U.S.C. 119 of Danish application no. PA 2000 00573 filed on Apr. 6, 2000 and U.S. provisional application No. 60/197,650 filed on Apr. 17, 2000, the contents of which are fully incorporated herein by reference.

FIELD OF THE INVENTION

The present invention relates to a method of shock heat treatment of polypeptides, to a stable polypeptide in a fluid medium, to a pharmaceutical composition comprising a stable polypeptide, to use of shock heat treatment for stabilizing a polypeptide, and to an industrial or large scale method of manufacturing a polypeptide comprising applying shock heat treatment during the manufacturing of said polypeptide.

BACKGROUND

Proteins are known to associate in solution. This association is termed aggregation, dimerization, polymerization, precipitation, emulsification, fibrillation, destabilization, inclusion body formation, and more, depending on the protein or the case story.

Changes in the association capabilities can be initiated by breaking of the weak linkages or bonds (e.g., hydrogen bonds), that exist within a protein molecule, and which is responsible for the highly ordered structure of the protein in its stable state. Such destabilized proteins have a looser, more random structure. Denaturation can be brought about in various ways, such as by heating, by vigorous shaking, by treatment with acid, detergents, or other additives. A common consequence of destabilization is loss of biological activity (e.g., loss of the catalytic activity/ability of an enzyme, loss of pharmacological effect of a drug).

The original structure of some proteins can be regenerated upon removal of the destabilizing factor and restoration of conditions favoring a stable state. However, in many cases regeneration is difficult. New techniques to improve such processes without loss of biological function are important.

Protein association is initiated and/or accompanied by structural changes of the protein, i.e. changes in the physical conformation. To be in control of such structural changes is of high importance, because the polypeptide hereby is stabilized.

DESCRIPTION OF THE INVENTION

It has been shown that a short periode of heating (herein designated shock heat treatment) of a protein sample can improve the protein stability without substantial loss of biological activity.

The invention can be used as a unit operation during preparation, purification, and/or formulation of polypeptides. Compared to other methods, it is advantageous that the method of the invention can be applied to change polypeptide conformation in a very fast and non-invasive manner.

In one aspect the invention relates to a method of stabilizing a polypeptide comprising shock heat treatment of said polypeptide.

In another aspect the invention relates to a method for decreasing the association of a polypeptide comprising shock heat treatment of said polypeptide.

In a further aspect the invention relates to a method for arresting the association of a polypeptide comprising shock heat treatment of said polypeptide.

In a further aspect the invention relates to a method for postponement of the association of a polypeptide comprising shock heat treatment of said polypeptide.

In a further aspect the invention relates to a method for prevention of the association of a polypeptide comprising shock heat treatment of said polypeptide.

In a further aspect the invention relates to a method of producing a storage stable polypeptide comprising shock heat treatment of said polypeptide.

In a further aspect the invention relates to a stable polypeptide in a fluid medium, obtainable by a method comprising shock heat treatment of said polypeptide.

In a further aspect the invention relates to a pharmaceutical composition comprising a stable polypeptide in a fluid medium, obtainable by a method comprising shock heat treatment of said polypeptide.

In a further aspect the invention relates to use of shock heat treatment for stabilizing a polypeptide.

In another aspect the invention relates to use of shock heat treatment for decreasing the association of a polypeptide.

In a further aspect the invention relates to use of shock heat treatment for arresting the association of a polypeptide.

In a further aspect the invention relates to use of shock heat treatment for postponement of the association of a polypeptide.

In a further aspect the invention relates to use of shock heat treatment for prevention of the association of a polypeptide.

In a further aspect the invention relates to use of shock heat treatment for producing a storage stable polypeptide.

Industrial or large scale methods of manufacturing polypeptides are intended to include the preparation of the polypeptides, such as by culturing or fermentation, or organic peptide synthesis, recovery of the polypeptides from the culture or from the reaction mixture, the purification of the polypeptides, optionally further modification of the polypeptides and/or formulation of the polypeptide for storage or for making a composition, e.g. a pharmaceutical drug or an industriel enzyme. During the industrial or large scale method of manufacturing a polypeptide, there are several possibilities of applying shock heat treatment, such as the use of a unit operation element, eg. a heating mantle, or internal heating element, e.g. a piezoelectrical element, during recovery and/or purification and/or modification of the polypeptide, or the use of a water bath during formulation of the polypeptide.

In a further aspect the invention relates to an industrial or large scale method of manufacturing a polypeptide comprising applying shock heat treatment during the manufacturing of said polypeptide.

In one embodiment of the invention the polypeptide is in a fluid medium. In another embodiment of the invention the fluid medium is a gas. In a further embodiment of the invention the fluid medium is a liquid. In a further embodiment of the invention the fluid medium is a solution. In a further embodiment of the invention the fluid medium is a suspension. In a further embodiment of the invention the fluid medium may be an organic medium. In a further embodiment of the invention the fluid medium may be an aqueous medium. Preferred examples of the fluid medium are an aqueous solution, aqueous suspension, organic gas, organic solution, or organic suspension, or any mixture thereof. Examples of organic solutions comprising the polypeptide are a $C_{1-6}$-alkanol, such as methanol, ethanol, 2-propanol, tert-butanol and n-butanol; acetonitril; $C_{3-12}$-ketones, e.g. acetone; diols, triols and polyols, e.g. glycerol; phenol; cresols, e.g. m-cresol. Examples of mixtures of an organic and aqueous medium are solutions or suspensions comprising water and a $C_{1-6}$-alkanol. Each of these fluid mediums constitutes an individual embodiment of the present invention.

In a further embodiment of the invention the shock heat treatment is done without changing the chemical structure of the polypeptide. In a further embodiment of the invention the shock heat treatment is done without changing the primary structure of the polypeptide. In a further embodiment of the invention the shock heat treatment is done without substantial loss, preferably without loss, of the biological activity of the polypeptide. In a further embodiment of the invention the shock heat treatment is done without substantial loss, preferably without loss, of the biological activity of the polypeptide, but the chemical structure, such as the primary structure, is changed. For instance, shock heat treatment may lead to deamidation of a protein, but the biological activity is maintained. Precursors and prodrugs of the polypeptide which may or may not have a biological activity are intended to be comprised within the scope of the invention even in such cases where the precursor or prodrug does not have a biological activity.

In a further embodiment of the invention the shock heat treatment is done by applying a heating source, such as a heating mantle, an internal heating element, e.g. a piezo-electrical element, or boiling water.

In a further embodiment of the invention the shock heat treatment is applied for such time which increases the stability of the polypeptide formulation significantly.

In a further embodiment of the invention the shock heat treatment is applied for such time which increases the stability of the polypeptide formulation at least 1%. In further embodiments of the invention the shock heat treatment is applied for such time which increases the stability of the polypeptide formulation at least 10%, such as at least 20%, 30%, 40%, 50%, or two-fold (100%), or three-fold, or even ten-fold or more. This is of course compared to the situation where the polypeptide has not been shock heat treated.

In a further embodiment of the invention the shock heat treatment is applied for 1 milliseconds to about 60 seconds. In further embodiments of the invention the shock heat treatment is applied for 1 second to 60 seconds, such as 5 to 60 seconds, 10 to 60 seconds, 15 to 60 seconds, 20 to 60 seconds, 30 to 60 seconds. During the shock heat treatment the temperature in the fluid medium comprising the polypeptide will usually not exceed 200° C. In a further embodiment of the invention the temperature in the fluid medium comprising the polypeptide will usually not exceed 150° C. In a further embodiment of the invention the temperature in the fluid medium comprising the polypeptide will usually not exceed 100° C. In a further embodiment of the invention the temperature in the fluid medium comprising the polypeptide will usually not exceed 90° C.

The heat effect and heat transfer depend on the size of the interface between the heating element and fluid, and also on the conductivity of the container means or unit operation element or parts therof, e.g. glas bottle, iron tube or pipe, glas tube or pipe or iron bottle, comprising the polypeptide in the fluid. For instance, a fluid in a long tube (e.g. chromatographic column, or a pipe connecting unit operation elements) will be heated faster than a fluid in a bottle (e.g. a vial), and the short time heating will have an increased effect in an iron container in relation to a glas container.

In a further embodiment of the invention the shock heat treatment is performed at a temperature rate in the fluid medium comprising the polypeptide of from about 0.1° C./second to about 100000° C./second. In further embodiments of the invention the temperature rate in the fluid medium comprising the polypeptide is from about 0.1° C./second to about 50000° C./second, 0.1° C./second to about 10000° C./second, 0.1° C./second to about 5000° C./second, 0.1° C./second to about 1000° C./second, 0.1° C./second to about 500° C./second, 0.1° C./second to about 100° C./second, 0.5° C./second to about 50° C./second, 1° C./second to about 10° C./second.

In a further embodiment of the invention the polypeptide is a drug or prodrug.

In a further embodiment of the invention the polypeptide comprises from two to five-hundred amino acid residues (hereinafter referred to as amino acids). In further embodiments of the invention the polypeptide comprises from 25 to 450 amino acids, such as 25 to 40 amino acids, 40 to 60 amino acids, 60 to 80 amino acids, 80 to 100 amino acids, 100 to 180 amino acids, 180 to 200 amino acids, 200 to 400 amino acids, 400 to 450 amino acids. Each of these suggested amino acid ranges constitutes an alternative embodiment of the present invention.

In a further embodiment of the invention the polypeptide comprises only natural amino acids.

In a further embodiment of the invention the polypeptide comprises posttranslational modified amino acids, wherein posttranslational modified amino acid is intended to mean amino acids which cannot be encoded by, e.g. DNA, or RNA.

In a further embodiment of the invention the polypeptide comprises both natural amino acids and posttranslational modified amino acids. Examples of natural amino acids are Ala, Cys, Asp, Glu, Phe, Gly, His, Ile, Lys, Leu, Met, Asn, Pro, Gin, Arg, Ser, Thr, Val, Trp, Tyr. Examples of posttranslational modified amino acids are β-Ala, D-Ala, D-Asp, D-Glu, D-Phe, D-His, Orn, D-Ser, Gla (4-carboxy glutamic acid or γ-carboxy glutamate), D-Cys, D-Asp, D-Ile, D-Lys, D-Leu, D-Met, D-Asn, D-Pro, D-Gln, D-Arg, D-Thr, D-Val, D-Trp, D-Tyr, hydroxyprolin, γ-amino butyric acid (GABA).

In a further embodiment of the invention the polypeptide is selected from peptides having at least two amino acids, such as oligopeptides, proteins, prions, amyloids, vira, as well as precursors, homologues, analogues and derivatives thereof. In a further embodiment of the invention the polypeptide is selected from glucagon, human growth hormone (hGH), human growth hormone binding protein, insulin, aprotinin, FactorVII, TPA, FactorVIIa, FactorVIIai, FFR-FactorVIIa, heparinase, ACTH, Heparin Binding Protein, corticotropin-releasing factor, angiotensin, calcitonin, insulin, glucagon-like peptide-1, glucagon-like peptide-2, insulin-like growth factor-1, insulin-like growth factor-2, fibroblast growth factors, gastric inhibitory peptide (GIP), growth hormone-releasing factor, pituitary adenylate cyclase activating peptides, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, DPP IV, interleukins, immunoglobulins, complement inhibitors, serpin protease inhibitors, cytokines, cytokine receptors, PDGF, tumor necrosis factors, tumor necrosis factors receptors, growth factors, exendins, e.g. exendin-3, exendin-4, peptide histidine-methionine amide, helospectins, helodermin, pituitary adenylate cyclase activating peptide-related peptide, or vasoactive intestinal polypeptide. It is intended that each of these peptides also includes precursors, homologues, analogues as well as derivatives thereof. In a further embodiment of the invention the polypeptide is selected from glucagon, human growth hormone, human growth hormone binding protein, insulin, aprotinin, FactorVII, FactorVIIa, FactorVIIai, FFR-FactorVIIa, heparinase, glucagon-like peptide-1, or glucagon-like peptide-2. Examples of such peptides are FactorVII, FactorVIIa, FactorVIIai, FFR-FactorVIIa, $Arg^{34}$, $Lys^{26}$(N-ε-(γ-Glu(N-α-hexadecanoyl)))-GLP-1(7-37), $Arg^{34}$GLP-1(7-37), $Val^8$-GLP-1(7-37), $Thr^8$-GLP-1(7-37), $Met^8$-GLP-1(7-37), $Gly^8$-GLP-1(7-37), $Arg^{26}$, $Lys^{34}$(N-ε-(γ-Glu(N-α-hexadecanoyl)))-GLP-1(7-37), GLP-2(1-33), humanGLP-2 (hGLP-2), glucagon(1-29), prothrombin, $Lys^{B29}$-(N-ε(α-tetradecanoyl))-desB30 insulin, aprotinin, human insulin, and B28IsoAsp insulin. Each of these polypeptides constitutes an alternative embodiment of the present invention.

In a further embodiment of the invention the polypeptide is selected from glucagon, insulin, GLP-1, GLP-2, GLP-1 (7-37), GLP-2(1-33), hGLP-2, hGH, Factor VII, Factor VIIa, Factor VIIai, or FFR-FactorVIIa. Each of these polypeptides constitutes an alternative embodiment of the present invention.

In a further embodiment of the invention the polypeptide is selected from a glucagon, an insulin, a GLP-1 analogue, or a GLP-2 analogue. Each of these polypeptides constitutes an alternative embodiment of the present invention.

In a further embodiment of the invention the polypeptide is selected from a glucagon, or an insulin, wherein the glucagon or insulin is human glucagon or human insulin, or is at least 90% homologues thereto, preferably 95% homologues thereto. Each of these polypeptides constitutes an alternative embodiment of the present invention.

In a further embodiment of the invention the polypeptide is selected from a GLP-1 analogue, wherein the GLP-1 analogue is humanGLP-1(7-37) or humanGLP-1(7-37) having one or two amino acid(s) substituted with a different amino acid selected from natural or post-translational modified amino acids. Each of these polypeptides constitutes an alternative embodiment of the present invention.

In a further embodiment of the invention the polypeptide is selected from a GLP-2 analogue, wherein the GLP-2 analogue is humanGLP-2 (1-33) or humanGLP-2 (1-33) having one or two amino acid(s) substituted with a different amino acid selected from natural or post-translational modified amino acids. Each of these polypeptides constitutes an alternative embodiment of the present invention.

Any possible combination of two or more of the embodiments described herein, is intended to be comprised within the scope of the present invention.

The polypeptides can be produced by a method which comprises culturing or fermenting a host cell containing a DNA sequence encoding the polypeptide and capable of expressing the polypeptide in a suitable nutrient medium under conditions permitting the expression of the peptide, after which the resulting peptide is recovered from the culture or fermentation broth. Hereinafter, culturing will be used to cover both culturing and fermenting and the like.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including, optionally lysis of cells, separating the host cells from the medium by centrifugation or filtration, precipitating the proteinaceous components of the supernatant or filtrate by means of a salt, e.g. ammonium sulphate, purification by conventional purification techniques, such as chromatographic techniques, if necessary, purification by ion exchange chromatography according to the present invention, and subsequently, subjecting to analytical tests, e.g. PAGE, IEF, if necessary, subjecting to further purification, if necessary, and isolation of the pure peptide.

During the recovery of the resulting peptide from the culture medium, but before purification by ion exchange chromatography according to the present invention, the mixture comprising the peptide and related impurities may optionally be chemically modified by conventional techniques, e.g. by alkylation, acylation, ester formation or amide formation or the like.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, EF and Maniatis, T, *Molecular Cloning: A Laboratory Manual*, Cold Spring Harbor Laboratory Press, New York, 1989). The DNA sequence encoding the peptide may also be prepared synthetically by established standard methods, e.g. the phosphoamidite method described by Beaucage and Caruthers, *Tetrahedron Letters* 22 (1981), 1859–1869, or the method described by Matthes et al., EMBO Journal 3 (1984), 801–805. The DNA sequence may also be prepared by polymerase chain reaction using specific primers, for instance as described in U.S. Pat No. 4,683,202 or Saiki et al., *Science* 239 (1988), 487–491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a peptide into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, vira, e.g. baculo virus, yeast, fungi, insect cells and higher eukaryotic cells. Examples of suitable host cells well known and used in the art are, without limitation, *E. coli, Saccharomyces cerevisiae,* or mammalian BHK or CHO cell lines.

Some of the peptides, in particular the oligopeptides, can be produced according to conventional organic peptide synthetic chemistry. The resulting synthetic mixture may then be chemically modified, e.g. by alkylation, acylation, ester formation or amide formation or the like, and purified, or purified as it is and then modified chemically as mentioned above.

Preparation of Factor VIIa (NovoSeven®, Available from Novo Nordisk A/S, Bagsvaerd, Denmark)

Human purified factor VIIa suitable for use in the present invention is preferably made by DNA recombinant technology, e.g. as described by Hagen et al., *Proc.Natl.Acad.Sci. USA* 83: 2412–2416, 1986 or as described in European Patent No. 200.421 (ZymoGenetics). Factor VIIa produced by recombinant technology may be authentic factor VIIa or a more or less modified factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, *J.Biol.Chem.* 255 (4): 1242–1247, 1980 and Hedner and Kisiel, *J.Clin.Invest.* 71: 1836–1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IX a or Xa. Alternatively, as described by Bjoern et al. (Research Disclosure, 269 September 1986, pp. 564–565), factor VII may be activated by passing it through an ion-exchange chromatography column, such as Mono Q® (Pharmacia fine Chemicals) or the like.

Modified or Inactivated FVIIa (FVIIai) may be Produced by the Following Methods

International Application No. WO 92/15686 relates to modified Factor VIIa, polynucleic acid and mammalian cell lines for the production of modified Factor VIIa, and compositions comprising modified Factor VIIa for inhibiting blood coagulation.

Modified Factor VII may be encoded by a polynucleotide molecule comprising two operatively linked sequence coding regions encoding, respectively, a pre-pro peptide and a gla domain of a vitamin K-dependent plasma protein, and a gla domain-less Factor VII protein, wherein upon expression said polynucleotide encodes a modified Factor VII molecule which does not significantly activate plasma Factors X or IX, and is capable of binding tissue factor.

The catalytic activity of Factor VIIa can be inhibited by chemical derivatization of the catalytic centre, or triad. Derivatization may be accomplished by reacting Factor VII with an irreversible inhibitor such as an organophosphor compound, a sulfonyl fluoride, a peptide halomethyl ketone or an azapeptide, or by acylation, for example. Preferred peptide halomethyl ketones include PPACK (D-Phe-Pro-Arg chloromethyl-ketone; (see U.S. Pat. No. 4,318,904, incorporated herein by reference), D-Phe-Phe-Arg and Phe-Phe-Arg chloromethylketone (FFR-cmk); and DEGRck (dansyl-Glu-Gly-Arg chloromethylketone).

The catalytic activity of Factor VIIa can also be inhibited by substituting, inserting or deleting amino acids. In preferred embodiments amino acid substitutions are made in the amino acid sequence of the Factor VII catalytic triad, defined herein as the regions, which contain the amino acids, which contribute to the Factor VIIa catalytic site. The substitutions, insertions or deletions in the catalytic triad are generally at or adjacent to the amino acids which form the catalytic site. In the human and bovine Factor VII proteins, the amino acids, which form a catalytic "triad", are $Ser_{344}$, $Asp_{242}$, and $His_{193}$ (subscript numbering indicating position in the sequence). The catalytic sites in Factor VII from other mammalian species may be determined using presently available techniques including, among others, protein isolation and amino acid sequence analysis. Catalytic sites may also be determined by aligning a sequence with the sequence of other serine proteases, particularly chymotrypsin, whose active site has been previously determined (Sigler et al., *J. Mol. Biol.,* 35:143–164 (1968), incorporated herein by reference), and there from determining from said alignment the analogous active site residues.

In preferred embodiments of human and bovine Factor VII, the active site residue $Ser_{344}$ is modified, replaced with Gly, Met, Thr, or more preferably, Ala. Such substitution could be made separately or in combination with substitution(s) at other sites in the catalytic triad, which includes $His_{193}$ and $Asp_{242}$.

The amino acids, which form the catalytic site in Factor VII, such as $Ser_{344}$, $Asp_{242}$, and $His_{193}$ in human and bovine Factor VII, may either be substituted or deleted. Within the present invention, it is preferred to change only a single amino acid, thus minimizing the likelihood of increasing the antigenicity of the molecule or inhibiting its ability to bind tissue factor, however two or more amino acid changes (substitutions, additions or deletions) may be made and combinations of substitution(s), addition(s) and deletion(s) may also be made. In a preferred embodiment for human and bovine Factor VII, $Ser_{344}$ is preferably substituted with Ala, but Gly, Met, Thr or other amino acids can be substituted. It is preferred to replace Asp with Glu and to replace His with Lys or Arg. In general, substitutions are chosen to disrupt the tertiary protein structure as little as possible. The model of Dayhoff et al. (in *Atlas of Protein Structure* 1978, Nat'l Biomed. Res. Found., Washington, D.C.), incorporated herein by reference, may be used as a guide in selecting other amino acid substitutions. One may introduce residue alterations as described above in the catalytic site of appropriate Factor VII sequence of human, bovine or other species and test the resulting protein for a desired level of inhibition of catalytic activity and resulting anticoagulant activity as described herein. For the modified Factor VII the catalytic activity will be substantially inhibited, generally less than about 5% of the catalytic activity of wild-type Factor VII of the corresponding species, more preferably less than about 1%.

The modified Factor VII may be produced through the use of recombinant DNA techniques.

The amino acid sequence alterations may be accomplished by a variety of techniques. Modification of the DNA sequence may be by site-specific mutagenesis. Techniques for site-specific mutagenesis are well known in the art and are described by, for example, Zoller and Smith (*DNA* 3:479–488, 1984). Thus, using the nucleotide and amino acid sequences of Factor VII, one may introduce the alteration(s) of choice.

The modified FVIIa may also be produced by chemical methods.

FFR-FVIIa (that is, D-Phe-Phe-Arg-FVIIa)
Blockage of the Active Site of FVIIa with FFR Chloromethyl Ketone.

Blockage of the active site serine and histidine with chloromethyl ketone is a well-known method for irreversible inactivation of serine proteases. In order to optimise the blockage of a given protease it is important to choose a chloromethyl ketone derivative, which reacts acts specifically with the active site and with a fast on-rate. Such derivatives can be developed by attachment to the chloromethyl ketone group of an oligopeptide, which interacts, with the substrate-binding pocket of the particular serine protease of interest.

Glutamyl-Glycyl-Arginine chloromethyl ketone (EGR-ck or its Dansyl derivative, DEGR-ck) (S. Higashi, H. Nishimura, S. Fujii, K. Takada, S. Iwanaga, (1992) J. Biol. Chem. 267, 17990) or Prolyl-Phenyl-Arginine chloromethyl ketone (PFR-ck) ( J. H. Lawson, S. Butenas, K. Mann, (1992) J. Biol. Chem. 267, 4834; J. Contrino, G. A. Hair, M. A. Schmeizl, F. R. Rickles, D. L. Kreutzer (1994) Am. J. Pathol. 145, 1315) have been applied as active site inhibitors of FVIIa. Compared with these chloromethyl ketones application of FFRck represents a rate increase of 10–70 fold.

The specificity of the reaction with FFR-chloromethyl ketone derivative of FVIIa was checked by HPLC and peptide mapping which showed that FVIIa had reacted with FFR-chloromethyl ketone in a 1:1 ratio such that >98% could be recovered as the expected product derivatized at histidine 193.

Inactivation of FVIIa by Various Chloromethyl Ketones

3 $\mu$M FVIIa was incubated with 12 $\mu$M of chloromethyl ketone derivative in 50 mM TrisHCl, 100 mM NaCl, 5 mM $CaCl_2$, 0.01% Tween-80, pH 7.4. Samples were withdrawn at various time intervals as indicated and and diluted 20 times for activity measurements in 50 mM TrisHCl, 100 mM NaCl, 5 mM $CaCl_2$, 0.01% Tween-80, pH 7.4 containing 1 mM Ile-Pro-Arg-pNA. The residual FVIIa activity was measured by the increase in absorbance at 405 nm.

Glucagon (29 amino acids; see e.g. *The Merck Index*, $10^{th}$ Edition for the amino acid sequence) and GLP-1 compounds (typically about 29–31 amino acids) are single chain highly homologous peptides (meaning about 45–50% homology). The physico-chemical properties of glucagon are well described in the literature (J.Biol.Chem. 244, 6675–6679 (1969); Nature 257, 751–757 (1975); FEBS Letts. 119, 265–270 (1980)).

Glucagon-Like Peptide-1 (GLP-1) (cf. Schmidt et al. in Diabetologia 28 704–707, 1985) and analogues as well as derivatives thereof may be used in the treatment of diabetes, as disclosed in WO 98/08871. WO 98/08871 discloses GLP-1 derivatives in which a lipophilic substituent is attached to at least one amino acid residue. The lipophilic substituents are in particular long-chain groups containing e.g. 12–24 carbon atoms. WO 87/06941 (The General Hospital Corporation) disclose peptide fragments which comprises GLP-1(7-37) and functional derivatives thereof and to its use as an insulinotropic agent. WO 90/11296 (The General Hospital Corporation) disclose peptide fragments which comprise GLP-1 (7-36) and functional derivatives thereof and have an insulinotropic activity which exceeds the insulinotropic activity of GLP-1(1-36) or GLP-1(1-37) and to their use as insulinotropic agents. WO 91/11457 (Buckley et al.) discloses analogues of the active GLP-1 peptides 7-34, 7-35, 7-36, and 7-37. EP 0699686 (Eli Lilly & Co.) discloses certain N-terminal truncated fragments of GLP-1 that are reported to be biologically active. EP 0708179-A2 (Eli Lilly & Co.) discloses GLP-1 analogues and derivatives that include an N-terminal imidazole group and optionally an unbranched $C_6$–$C_{10}$ acyl group in attached to the lysine residue in position 34.

WO 98/08872 discloses GLP-2 derivatives in which a lipophilic substituent is attached to at least one amino acid residue. The lipophilic substituents are in particular long-chain groups containing e.g. 12–24 carbon atoms. WO 96/32414 discloses GLP-2 analogues, according to the description GLP-2 is effective as a gastrointestinal tissue growth factor.

EP 214826 discloses insulin analogues with improved properties for treatment of diabetes. U.S. Pat No. 4,946,828 discloses insulin analogues and derivatives with improved properties for treatment of diabetes. EP 254516 discloses insulin analogues and derivatives with improved properties for treatment of diabetes. EP 280534 discloses insulin derivatives with improved properties for treatment of diabetes. EP 837072 discloses insulin analogues with improved properties for treatment of diabetes.

The term "polypeptide", as used herein, is intended to include such peptides having at least two amino acids, including oligopeptides, proteins, prions, amyloids, vira, as well as precursors, homologues, analogues and derivatives thereof, which are capable of being produced by conventional recombinant DNA techniques as well as conventional organic synthetic methods. When a specific polypeptide is mentioned it is also intended to include precursors. Such peptides include but are not limited to glucagon, growth hormone, e.g. human growth hormone, human growth hormone binding protein, insulin, aprotinin, FactorVII, TPA, FactorVIIa, FactorVIIai, FFR-FactorVIIa, heparinase, ACTH, Heparin Binding Protein, corticotropin-releasing factor, angiotensin, calcitonin, insulin, glucagon-like peptide-1, glucagon-like peptide-2, insulin-like growth factor-1, insulin-like growth factor-2, fibroblast growth factors, gastric inhibitory peptide (GIP), growth hormone-releasing factor, pituitary adenylate cyclase activating peptides, secretin, enterogastrin, somatostatin, somatotropin, somatomedin, para-thyroid hormone, thrombopoietin, erythropoietin, hypothalamic releasing factors, prolactin, thyroid stimulating hormones, endorphins, enkephalins, vasopressin, oxytocin, opiods, DPP IV, interleukins, immunoglobulins, complement inhibitors, serpin protease inhibitors, cytokines, cytokine receptors, PDGF, tumor necrosis factors, tumor necrosis factors receptors, growth factors, exendins, peptide histidine-methionine amide, helospectins, helodermin, pituitary adenylate cyclase activating peptide-related peptide, vasoactive intestinal polypeptide and precursors, homologues, analogues and/or derivatives thereof. Precursors are used to designate a peptide from which another peptide, such as any one of the above peptides, which usually is more active and/or more mature is formed. Homologues are used to designate a peptide which shows at least 50% homology, such as at least 70% homology, with a peptide, such as any one of the above peptides, to which it is compared. Analogues are used to designate a peptide, such as any one of the above peptides, wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both. Derivatives are used in the present text to designate a peptide, such as any one of the above peptides, in which one or more of the amino acid residues of the parent peptide have been chemically modified, e.g. by alkylation, acylation, ester formation or amide formation or the like. Derivatives is also intended to comprise peptides which are glycosylated.

In the present context "a polypeptide" is also intended to comprise active metabolites and prodrugs thereof, such as active metabolites and prodrugs of peptides including but not limited to glucagon, insulin, GLP-1, GLP-2, hGH, Factor VII, Factor VIIa, Factor VIIai or an analogue or a derivative thereof. A "metabolite" is an active derivative of a polypeptide produced when the polypeptide is metabolized. A "prodrug" is a compound which is either metabolized to a polypeptide or is metabolized to the same metabolite(s) as a polypeptide.

The term "stabilizing a polypeptide", as used herein, is intended to indicate that the association of the polypeptide, such as aggregation, dimerization, polymerization, precipitation, emulsification, fibrillation, destabilization, and/or inclusion body formation, has been prevented, postponed, decreased, or arrested, thereby consolidating polypeptide conformation, enhancing polypeptide stability, including storage stability, and/or improving polypeptide folding/unfolding pathways, and thus, be in control during the handling and/or manufacturing of the polypeptides. Association of a polypeptide can be detected in many ways, for instance, association can result in changes in the secondary structure of the protein (e.g. changes in spectroscopic profiles and nuclear magnetic resonances, as seen by e.g. ultraviolet (UV), Circular Dichroism (CD), Fourier transformed infrared (FTIR), infrared (IR), or nuclear magnetic resonance (NMR)), in increased apparent molecular size (e.g. increased retention in gel permeation, as seen by gel electrophoresis and gel permeation chromatography, and increased sedimentation speed, as seen by ultra-centrifugation), in decreased molecular mobility in water and other solvents (e.g. smaller diffusion coefficient, as seen in by light scattering), and/or in increased solution thickness (e.g. increased dynamic viscosity of solution, as seen by rheological techniques).

The term "shock heat treatment", as used herein, is intended to mean the application of heat from a heating source, such as boiling water, heating mantle, internal heating element (e.g. piezoelectrical crystals), and the like, or from the convertion of other energy forms into heat, such as the application of electromagnetic radiation, for a limited time period, which increases the stability of the polypeptide in a fluid medium. Such time period is typically from a few milliseconds to about 60 seconds, and the temperature in the fluid medium comprising the polypeptide will usually not exceed 100° C., since that may denature the polypeptide. The temperature rate in the fluid medium comprising the polypeptide is typically from about 0.1° C./second to about 100° C./second.

The term "a fluid medium", as used herein, is intended to mean, a gas or liquid medium, wherein the liquid is a solution or suspension. The fluid medium may be an organic or an aqueous medium, or a mixture thereof, such as an aqueous solution, aqueous suspension, organic solution, or organic suspension, or any mixture thereof.

EXAMPLES

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLE 1

Inhibition of Glucagon Fibrillation

Glucagon (expressed in *S.cerevisiae*) in solution easily associates into insoluble fibrils. This comprises severe technical problems during industrial purification and analysis of this drug. Measuring the dynamic viscosity of a glucagon solution versus time can be used for monitoring glucagon fibrillation capacity.

Dissolved samples of easily fibrillating glucagon (5 mg/ml, pH=3.0, in 150 mM NaCl) were investigated in a rheometer (Brookfield DV-III, cup CP-40; shear rate 500 $s^{-1}$, temperature 25° C).

FIG. 1 indicates the dynamic viscosity of freshly prepared samples increased from 1 mPa·s to 5 mPa·s (25° C.) within 5–10 minutes. Samples from the same batches were heat-treated for 30 s (max temperature 80° C.). The viscosity of these heat-treated samples now increased from 1 mPa·s to 5 mPa·s (25° C.) within 25–30 minutes.

The chemical structure of the protein was unchanged after the heat-treatment, as seen by automatizied Edman degradation, followed by N-terminal sequence analysis (Applied Biosystems Model 494A), and as seen by reversed phase chromatography at pH=2.5 (5 μm, C18 silica based, 45° C., solvent: 30%/70% acetonitril/water).

EXAMPLE 2

Prolonged Storage Stability of Insulin Penfill®

Human insulin in formulations for injection associates with time. The storage stability of insulin in Penfill® is limited due to this association (Penfill® is available from Novo Nordisk A/S, Bagsvaerd, DK). Penfill® samples is heat-treated for short periods of time to obtain temperatures of 50° C. to 90° C. for less than 1 min. After storage for 2 weeks at controlled shaking at 25° C., the mean molecular mobility in heat-treated Penfill® will be lower than the mean molecular mobility in non-heat-treated Penfill®, indicating that the association capacity has been reduced.

EXAMPLE 3

Recovery of a Fibrillated Glucagon-like-peptide-1 Analogue (R34-GLP1)

Arg34-GLP-1(7-37) (hereinafter R34-GLP1) is expressed in *S.cerevisiae*, and purified by a series of chromatography steps. Intermediate products might occasionally fibrillate into highly stable precipitates. Traditional recovery methods applied for glucagon have proven to be ineffective.

Precipitated R34-GLP1 was measured in a Rheometer (Brookfield DV-III, cup CP-40; shear rate 500 $s^{-1}$) at pH=9.0 (25° C.). The sample is highly imhomogeneous with viscosity higher than 5 mPas.

After adjustment of acidity to pH=11.5 (25° C.), the R34-GLP1 solution becomes less viscious, however, fibrils and precipitates do not dissolve. Fibrillated R34-GLP1, adjusted to pH=11.5, is heat-treated for a short period (less than 30 sek, max temperature 80° C.), and solution clarifies. Viscosity decreases to that of saline water. Stable solution is retained after adjustment to pH=9.0. Storage stability has increased from less than one day to several days (4° C.).

The chemical structure of the protein is unchanged after the heat-treatment, as seen by automatizied Edman degradation, followed by N-terminal sequence analysis (Applied Biosystems Model 494A), and as seen by reversed phase chromatography at pH=2.5 (5 μm, C18 silica based, 45° C., solvent: 30%/70% acetonitril/water).

What is claimed is:

1. A method of stabilizing a polypeptide, said method comprising subjecting said polypeptide to heat treatment under conditions effective for stabilizing said polypeptide, wherein said conditions comprise treatment for 1 milliseconds to 60 seconds at a temperature not exceeding 100° C. and wherein said polypeptide is selected from the group consisting of glucagon, insulin, glucagon-like peptide-1 (GLP-1), glucagon-like peptide-2 (GLP-2), and analogues thereof.

2. The method of claim 1 wherein said polypeptide is in a fluid medium.

3. A pharmaceutical composition comprising a polypeptide stabilized using a method as defined in claim 1, wherein said polypeptide is selected from the group consisting of glucagon, insulin, glucagon-like peptide-1 (GLP-1), glucagon-like peptide-2 (GLP-2), and analogues thereof.

* * * * *